(12) United States Patent
Greenspan

(10) Patent No.: US 8,843,202 B2
(45) Date of Patent: *Sep. 23, 2014

(54) OCCIPITAL NEUROMODULATION METHOD

(71) Applicant: Joshua Greenspan, Portsmouth, NH (US)

(72) Inventor: Joshua Greenspan, Portsmouth, NH (US)

(*) Notice: Subject to any disclaimer, the term of this patent is extended or adjusted under 35 U.S.C. 154(b) by 64 days.

This patent is subject to a terminal disclaimer.

(21) Appl. No.: 13/632,180

(22) Filed: Oct. 1, 2012

(65) Prior Publication Data

US 2013/0023951 A1    Jan. 24, 2013

Related U.S. Application Data

(63) Continuation-in-part of application No. 12/211,411, filed on Sep. 16, 2008, now Pat. No. 8,280,515.

(51) Int. Cl.
A61N 1/05     (2006.01)
A61N 1/36     (2006.01)

(52) U.S. Cl.
CPC .......... *A61N 1/0534* (2013.01); *A61N 1/36017* (2013.01); *A61N 1/36175* (2013.01); *A61N 1/36071* (2013.01); *A61N 1/0504* (2013.01); *A61N 1/36171* (2013.01); *A61N 1/36025* (2013.01); *A61N 1/36082* (2013.01); *A61N 1/36157* (2013.01); *A61N 1/36075* (2013.01)
USPC .......................................................... 607/46

(58) Field of Classification Search
USPC .......................................................... 607/46
See application file for complete search history.

(56) References Cited

U.S. PATENT DOCUMENTS 8,280,515 B2 * 10/2012 Greenspan ...................... 607/46
2006/0161219 A1    7/2006 Mock et al.
2009/0082829 A1 *  3/2009 Panken et al. .................. 607/45
2010/0069995 A1 *  3/2010 Danielsson ..................... 607/50

OTHER PUBLICATIONS

Chinese State Intellectual Property Office, Office Action in Chinese Patent Application (May 2009).

* cited by examiner

Primary Examiner — Eric D. Bertram
(74) Attorney, Agent, or Firm — Mesmer & Deleault, PLLC

(57) ABSTRACT

A method of treating pain in a subject includes the step of positioning a tip of one or more leads subcutaneously in the occipital region of a subject's scalp, where the leads are configured to conduct an electrical signal along an occipital nerve into the brain. The leads are energized to conduct the electrical signal along the occipital nerve and the electrical signal is adjusted to a level effective to decrease the subject's pain over time and so that the subject cannot feel the lead being energized.

11 Claims, 5 Drawing Sheets

OCCIPITAL NEUROMODULATION METHOD

This application is a continuation-in-part of U.S. application Ser. No. 12/211,411 filed Sep. 16, 2008, now U.S. Pat. No. 8,280,515 (issue date Oct. 2, 2012).

BACKGROUND

1. Field of the Invention

This invention relates to the treatment of pain in humans using electrical pulses.

2. Description of the Related Art

A background of knowledge is required to adequately understand occipital neuromodulation. The following is an attempt to summarize this knowledge.

Pain is a form of sensory input that is conveyed to the brain via our nervous system. Within the brain, pain is processed within discrete processing centers. These discrete processing centers are being discovered through the use of functional MRI and PET scans which show the metabolic activity within the brain. One can see how active a given area of the brain is by looking at its metabolic activity. Areas that are quiescent have lower metabolic activity compared with those that are active. With the use of such imaging modalities, a map is made of the metabolic activity within the brain. That baseline map of activity can then be compared to that seen when various types of sensory input are applied to a test subject. It is therefore possible to demonstrate changes within the brain caused by specific activities or forms of sensory stimulation. Furthermore one can observe changes in the brain when those specific activities or forms of stimulation are withdrawn.

The nervous system involves both electrical and chemical activity. There is both electrical activity involving the transmission of electrical signals, as well as the balance of chemical agents known collectively as neurotransmitters. There is a direct relationship between neurotransmitters and the transmission of electrical activity. Certain neurotransmitters increase or potentiate electrical activity. Others decrease or suppress electrical activity. For the purpose of this invention, neuromodulation is the act of using electrical signals from a peripheral nerve outside the brain to alter the balance of neurotransmitters within the brain.

The processing of pain information in discrete areas of the brain leads to alterations in other regions of the brain which makes this information manifest in what we consider our perception. The communication between the processing centers and these other regions occurs both on an electrical level and on a chemical level (nerves and neurotransmitters). As an illustration, patients with intractable depression respond to electroconvulsive therapy. By repeatedly inducing a massive electrical charge over the brain, the electrical system is reset and the depression alleviated via a change in the balance of neurotransmitters.

Yet another example is vision. To illustrate, we can easily read misspelled words as long as the first and last letters in each word are correct. Recently, a popular e-mail has circulated demonstrating this phenomenon of which many people have already seen. We can read such misspelled words since the processing centers for vision within our brains corrects the misspelled words.

The sensation of pain has been studied in this fashion. There is a growing body of literature surrounding this idea of the true nature of pain. A recent study was published by Dr. Marwan Balicki in The Journal of Neuroscience, Feb. 6, 2008. The authors of the study used functional MRI scans on both people with chronic pain and without and mapped out the differences in metabolic activity within the brain. What they found was that areas of the brain that were normally quiet in people when concentrating on a television screen were still active in the patients with chronic pain. These areas involved the processing of pain. When people without pain watched the television, these areas of the brain were metabolically quiet (like an engine in neutral). When patients with chronic pain watched the television, these areas of the brain were abnormally metabolically active (like an engine that was running at high RPM's).

There has also been recent research regarding the use of mirrors to relieve phantom limb pain. Apparently, when an amputee holds a mirror to create the visual illusion of having two normal limbs and moves the remaining limb, the brain processes the information in such a way so as to alleviate the pain coming from the missing limb. Through the use of creating an illusion of an intact limb, the processing of pain within the brain normalizes. A recent study in the New England Journal of Medicine elucidates this further: Chan B L, Witt R, Charrow A P, Magee A, Howard R, Pasquina P F, Heilman K M, Tsao J W Mirror Therapy for Phantom Limb Pain, New England Journal of Medicine, Nov. 22, 2007.

Functional MRI studies with patients with fibromyalgia also show abnormalities compared with normal controls. In a study performed by Williams and Gracely in Arthritis Research & Therapy 2006 using Functional MRI, the authors clearly showed abnormally increased metabolic activity in the processing centers for pain in patients with fibromyalgia. Fibromyalgia patients feel pain initially in one section of their bodies but over the years, the sensation of pain spreads across their bodies. Diagnostic tests of these painful areas such as X-rays and conventional MRI's show no pathology in the muscles or joints, but the pain persists. The term fibromyalgia is now considered as a misnomer since this pain syndrome is a central pain syndrome within the brain and has nothing to do with the fibrous or muscular tissue denoted by the meaning of the word "fibromyalgia". Occipital neuromodulation has been used to successfully treat the pain of fibromyalgia.

There is a study using stimulation of occipital nerves which demonstrated alterations in metabolic activity within the brain which was different depending on whether the device was active or not. The Neurosurgery and Neuroscience Divisions at the National Hospital for Neurology and Neurosurgery in London in conjunction with the Department of Neurosurgery in Dallas performed PET scan studies in 2004 on patients with traditional occipital stimulators. Matharu et al., infra. The studies found that occipital stimulation alters metabolic activity in the anterior cingulate cortex, left pulvinar, and dorsal rostral pons. These areas are considered to be the processing areas for pain.

The current belief is that chronic pain results in an electrical and chemical restructuring within the brain to promote the continued perception of pain. Even when the original anatomical cause for the pain has healed or has been surgically corrected, the pain may initially improve, but then returns. In many cases, the pain is unaltered despite the correction of the anatomical cause. In the field of pain management, this phenomenon is known as the "centralization of pain." The pain persists due to alterations in the processing centers for pain.

With this background, we will proceed to the technical aspects of occipital neuromodulation. Occipital neuromodulation is a significant improvement of the technology of spinal cord stimulation that has been in use since 1967. The concept behind spinal cord stimulation was that by imposing an external electrical field over the spinal cord, the transmission of pain signals to the brain could be interrupted, and thus relieve pain. Over the years, the technology became more advanced and the equipment became smaller. Approximately 17 years ago, it became possible to use the same equipment to stimulate small peripheral nerves and thus the discipline of peripheral nerve stimulation came into vogue. Approximately 16 years ago, physicians started using this equipment to stimulate the occipital nerves which are sensory nerves that run up the back of the head (the occipital region) to relieve the pain of migraines. For a number of years prior, it had been demonstrated that blocking the occipital nerves with local anesthesia could stop a migraine and reduce the frequency of its reoccurrence. This showed a link between the occipital nerves and migraines. So with that link in mind, physicians began using occipital stimulators to relieve migraines.

But it is much more complicated than that. In 2004 there was a study published in Brain, Volume 127, No. 1 pp. 220-230 by Matharu et al. In the study there were eight patients who had peripheral occipital nerve stimulators for chronic migraines. Each patient had two PET scans performed to map out the metabolic activity in the brain. One scan was performed with the device off, the second with the device on. There was a consistent pattern in changes in the metabolic activity within the pain processing centers in each of the eight patients. Therefore, the stimulation of a peripheral nerve was shown to cause changes within the brain itself. By stimulating a peripheral nerve electrically, there was a change in activity reflected in the pain processing areas within the brain.

One non-drug method that has been tried is disclosed in U.S. Pat. App. Pub. No. 2008/0045776 A1, by Fischell et al, published on Feb. 21, 2008, and which is not admitted to being prior art by its mention in this Background section. Fischell discloses a method and apparatus of treating headaches using a head-mounted magnetic depolarizer to generate a high intensity magnetic field around the user's head or neck. The depolarizer can be placed over the occipital region to generate a magnetic field one centimeter below the skin with a force between 0.1 and 5 Tesla. The purpose is to depolarize the neurons of the trigeminal nerve for terminating a migraine and other types of headaches after onset of aura but before the full migraine occurs. Although the apparatus is non-invasive, it is not suited for wearing on the body for more than a short period of time. In addition, it only treats headaches, and not other painful neurological ailments.

An apparatus that has been tried is disclosed in U.S. Pat. App. Pub. No. 2006/0074450 A1, by Boveja et al., published on Apr. 6, 2006, and which is not admitted to being prior art by its mention in this Background section. Boveja discloses a system for stimulating nerves or muscles to treat a variety of conditions, including occipital neuralgia and transformed migraine. However, the electrical signals used reveal that the system "stimulates" nerves in the sense that pain signals are overpowered and the subject will feel a tingling sensation. Although feeling the tingling is probably better than feeling pain, it would be advantageous if the system relieved pain without imposing a tingling sensation on the subject.

A method that has been tried is disclosed in "Central Neuromodulation in Chronic Migraine Patients With SubOccipital Stimulators: A PET Study," Brain, Vol. 127, No. 1, Nov. 7, 2003, pp. 220-230, by Matharu et al., which is not admitted to being prior art by its mention in this Background Section. Matharu taught the use of sub-occipital simulators for the treatment of migraine only. The electrical signals had a pulse width between 90 and 180 msec, frequency between 60 and 130 Hz, and amplitude between 1.5 and 10.5 V. The electrodes were positioned superficial to the cervical muscular fascia and transverse to the greater occipital nerve trunk at the level of the first cervical vertebrae (an anatomically different location than that used in occipital neuromodulation). One of the findings was that stimulator-induced paresthesia relieved pain.

Another method is disclosed in "Neuromodulation of the Occipital Nerve in Pain Management," Techniques in Regional Anesthesia and Pain Management, Vol. 10, No. 1, January 2006, pp. 10, 12-15, by Vallejo et al., and which is not admitted to being prior art by its mention in this Background section. This paper discloses a procedure for electrically stimulating the occipital nerve with electrodes coupled with an external programmable generator. The process treats occipital neuralgia. The paper does not define "neuromodulation" or provide any specific information about the composition of the electrical signal. However, since the process is performed with the patient awake and includes searching the patient's reported paresthesia (feeling the tingling sensation) in the areas of the pain (Id. at p. 14), one may conclude that the process stimulates the nerve well beyond the threshold to evoke the sensation of paresthesia.

Another system and method that has been tried is disclosed in U.S. Pat. App. Pub. No. 2006/0047325, by Thimineur et al, published on Mar. 2, 2006. This patent application is not admitted to being prior art by its mention in this Background section. Thimineur claims his device and process can block the perception of pain throughout the body, improve motor coordination, treat mental retardation, autism, Alzheimer's dementia, Parkinson's, pathological gambling, schizophrenia, postoperative ileus, Crohn's disease, rheumatoid arthritis, systemic lupus erythematosus, asthma, pituitary tumors, endometriosis, infertility, atherosclerotic cardiac disease, valvular heart disease, heart attacks, hypercholesterolemia, hypertension, diabetes, etc. His electrical stimulation parameters are a pulse width between 5 and 200 msec, frequency between 3 and 50 Hz, and amplitude between 2 and 100 mA. He claims to block pain by stimulating the spinal cord at the level of C2 (the second cervical vertebrae—an entirely different anatomical location from that of the present invention). A single pair of leads is used which is different than the present invention. Thimineur sets the device to cycle on and off (e.g. one minute on, ten minutes off).

Also, in the Thimineur method, the right and left leads are programmed identically with the same amplitudes. Therefore the power output from the right lead is always set the same as the left. It has been found however, that such parameters inevitably result in an imbalance of energy actually being delivered to the targeted nerves. The distance of each individual lead to its targeted nerve is different from the right side of the head to left side of the head. The scar tissue that develops from surgery and insulates each lead is also different from right to left. The scar tissue continues to grow over time and thus continues to create differences as well. The success rate of Thimineur's method has been reported to be 66%.

SUMMARY OF THE INVENTION

This is an invention that satisfies the need for a method, and apparatus, and a mechanism of action. This invention uses a spinal cord stimulator/peripheral nerve stimulator in a non-obvious manner to normalize the processing of pain information within the brain. This invention has been shown to result in relief of chronic intractable pain and is documented both in the medical records of these patients and in video testimony given by these patients. Occipital Neuromodulation has been performed on over 200 actual patients with a 90% success rate of the trials. If a trial is successful, the patients are implanted. Of the patients who have been implanted, over 95% of them still report greater than 80% relief after 2 years.

The method of treatment model involves two phases: a temporary or trial phase in which one pair of leads containing electrodes are placed under the skin proximal to the targeted neural tissue for days to weeks. This trial phase is to test the efficacy of the device and procedure for the patient. The leads are connected to an external power source with a computer to enable programming of the leads. At the end of the trial phase, the leads are removed. If the device was effective, the patient then goes on to have two sets of two leads (4 leads in total) placed surgically under the skin that are attached to an internal pulse generator. The internal pulse generator is a battery with a computer that enables programming of the individual electrodes within the leads. This is akin to a pacemaker. In the future, when battery technology advances enough, the leads and internal pulse generator will be a single unit. The present invention satisfies the need for a method and apparatus for modulating the signals sent to the brain's pain processing centers to have an effect upon the activity of neurotransmitters, which in turn will produce pain relief.

In one embodiment of the method, the tip of at least one lead subcutaneously is positioned in an occipital region of a subject's scalp, where the at least one lead configured to conduct an electrical signal along an occipital nerve into the brain. The lead(s) are energized to conduct the electrical signal along the occipital nerve into the brain and the electrical signal is adjusted to a level effective to decrease the subject's pain over time and where the subject cannot feel the lead being energized.

In another embodiment of the method, the leads include a first pair of leads having a first left lead and a first right lead, where the first left lead and the second left lead are positioned in opposite lateral occipital portions of the occipital region of the subject's scalp and along an imaginary line connecting the tops of the subject's ears. A second pair of leads is included and has a second left lead and a second right lead. The second pair of leads positioned below and substantially parallel to the imaginary line and wherein the second left lead and the second right lead are positioned in opposite lateral occipital portions of the occipital region of the subject's scalp.

In another embodiment of the method, the electrical signal has a current between 0.1 mA and 8 mA, a frequency between 4 Hz and 96 Hz, and a pulse width from 50 msec to 100 msec. In one embodiment, the current is 0.6 mA or below. In another embodiment, the frequency is 16 Hz and the pulse width is 100 msec. In yet another embodiment, the frequency is 96 Hz and the pulse width is 100 msec.

In another embodiment of the method, the electrical signal alters the release of one or more neurotransmitters within the brain, such as dopamine, serotonin, GABA, acetylcholine, and substance P.

In another embodiment, the method is used to treat migraine pain, fibromyalgia pain, neuropathic pain, and traumatic brain injury pain.

Another embodiment of the method includes the steps of coupling a programmer to the leads, where the programmer is capable of delivering the electrical signal to the occipital nerve to enable the subject to adjust the electrical signal to a level where the subject experiences a decrease in pain over time although not being able to feel the lead being energized. In this embodiment, the leads include a first temporary lead positioned in a first lateral occipital region substantially along an imaginary line connecting the tops of the subject's ears and a second temporary lead positioned in a second lateral occipital region opposing the first lateral occipital region and substantially along the imaginary line.

Another embodiment of the method includes implanting a first pair of permanent leads having a first left lead and a first right lead, where the first left lead and the first right lead are positioned in opposite lateral portions of the occipital region of the subject's scalp and along an imaginary line connecting the tops of the subject's ears. Also included is the step of implanting a second pair of permanent leads having a second left lead and a second right lead. The second pair of permanent leads is positioned below and substantially parallel to the imaginary line, where the second left lead and the second right lead are positioned in opposite lateral occipital portions of the occipital region of the subject's scalp. Also included are the steps of implanting an internal pulse generator subcutaneously and coupling the first pair of permanent leads and the second pair of permanent leads to the implanted internal pulse generator.

In another embodiment, the method also includes conducting a PET scan prior to the energizing step to establish a first metabolic activity level for pain centers within the brain, conducting a subsequent PET scan after the energizing step to determine a second metabolic activity level for pain centers within the brain, and comparing the second metabolic activity level with the first metabolic activity level to determine a change in metabolic activity.

In one embodiment of a neuromodulation kit for treating pain, the kit includes at least one pair of leads configured to conduct an electrical signal along an occipital nerve to alter the release of neurotransmitters within the brain, a pulse generator capable of energizing the leads with a neuromodulation signal having a current between 0.1 mA and 8 mA, a frequency from about 4 Hz to about 96 Hz, and a pulse width from 50 msec to 100 msec. The kit also includes instructions for programming the pulse generator to generate an electrical signal effective to treat pain using neuromodulation and below the level where the subject can feel the lead being energized, and for implanting the at least one pair of leads subcutaneously in respective opposite lateral portions of an occipital region of a subject's scalp. In another embodiment of the kit, the leads and the pulse generator comprise a single unit. In another embodiment of the kit, the single unit includes a battery.

DETAILED DESCRIPTION

Figure 1:
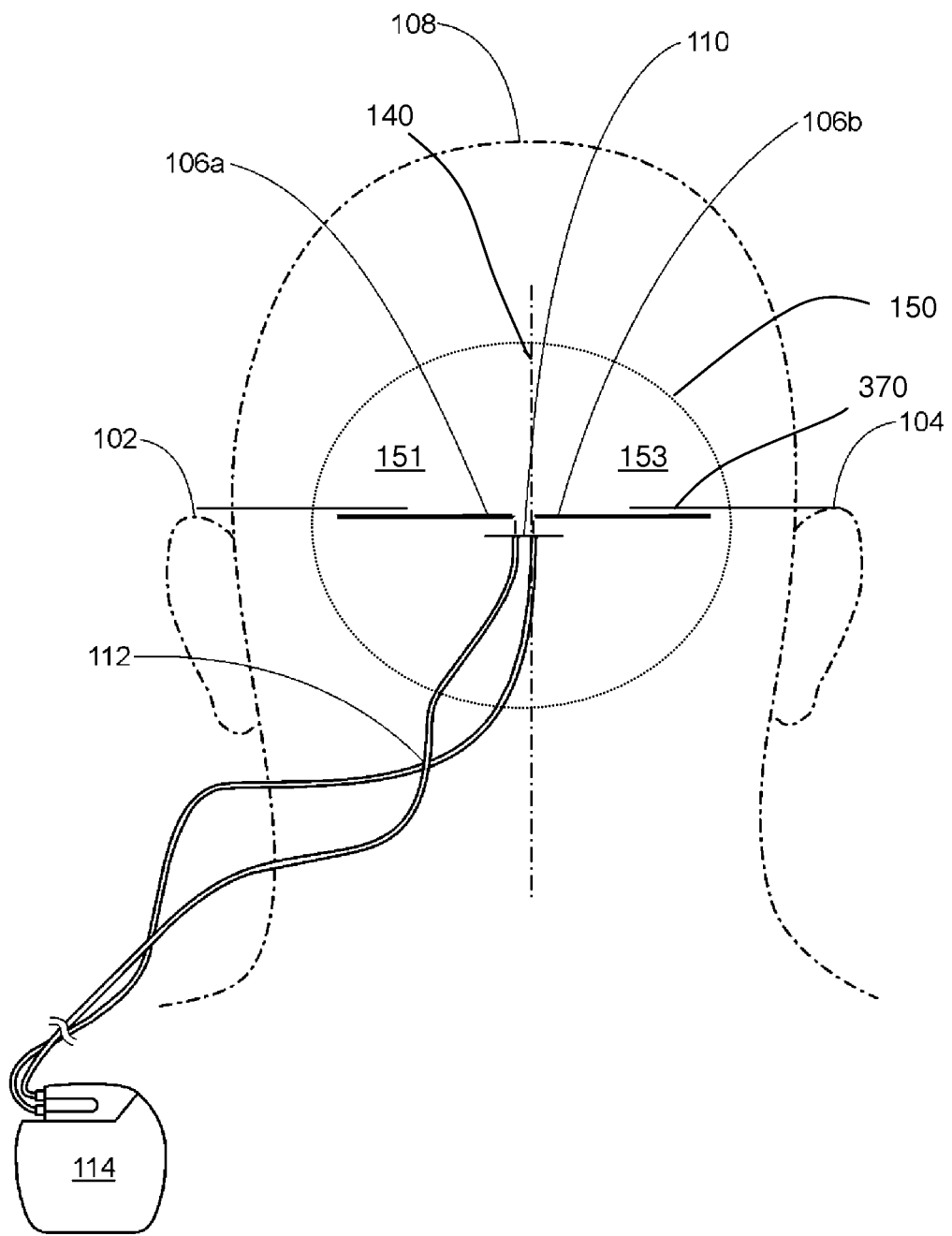
FIG. 1 shows the leads placed on a subject's head coupled with an external pulse generator during the trial phase.

The present invention is a method of occipital neuromodulation for the treatment of pain. This Detailed Description will first describe how the invention works. Then specific examples and discussion of the drawings will follow.

As used in this specification and claims, and as understood and used by practicing physicians, nurses, surgeons, and other medically-trained professionals, the word "subcutaneous" means "just below the skin." The term subcutaneous refers to the medically-defined tissue layer of the human body which lays beneath (sub) the surface of the skin (cutaneous), but does not extend as deep as the bones or into veins.

In contrast, the term "intracranial" refers to locations within (intra) the skull (cranial), and excludes locations referred to by the term "subcutaneous." Also, the term "intravascular" refers to locations within (intra) the blood vessels and lymphatics (vascular) and excludes locations referred to by the term "subcutaneous." The locations referenced by the terms "intracranial," "intravascular," and "subcutaneous" do not overlap and each term refers to different locations of the human body. For example, there are sutures designed to stitch vascular objects (blood vessels), and there are sutures designed to stitch subcutaneous tissue.

As used in this specification and claims, "neuromodulation" means the process in which the application of an external electrical field over neural tissue influences the perception of pain by altering the release of various neurotransmitters within the brain. Neuromodulation alters neural activity without destroying neural tissue. Altering the release of neurotransmitters such as dopamine, serotonin, GABA, acetylcholine, and substance P regulates diverse regions of neurons in the brain. With respect to pain, the neurotransmitters calm down the activity within these diverse regions of neurons in the brain. This results in the normalizing of the processing of pain information. In patients with chronic pain, these processing centers are hyperactive and produce the perception of pain.

As defined in this specification and claims, "neurostimulation" is decidedly different from "neuromodulation." Neurostimulation is the process in which the application of an external electrical field over neural tissue which interferes with pain transmission from that specific neural tissue. Neurostimulation therefore "masks" the pain being produced from that specific neural tissue. The specific neural tissue can be a peripheral nerve, or the spinal cord. The application of the external electrical field interferes with the neural tissues ability to transmit pain signals.

The mechanism for occipital neuromodulation is entirely different compared with occipital stimulation and is the focus of this patent specification. Peripheral nerve stimulators stimulate peripheral nerves to block or mask pain transmission. In occipital neuromodulation, there is no stimulation occurring. What is happening is that energy is conducted along the occipital nerves into the brain. Unlike occipital stimulation, the amount of energy is too small to be perceived by the patient. Within the brain, the electrical signals spread to the various processing centers for pain and alter the release of neurotransmitters. The neurotransmitters then alter the activity of the processing centers for pain. In patients with chronic pain, these processing centers can become pathological; showing abnormal activity as seen in the aforementioned functional MRI and PET scan studies. These areas are not being stimulated or activated; rather their activity is being modulated and adjusted to return to their normal state. This is why the term "neuromodulation" is being used to differentiate it from "stimulation."

With occipital neuromodulation, a change in metabolic activity can be observed using a PET scan. Compared to a baseline level of metabolic activity observed with the device inactive, a PET scan would show a change in metabolic activity when the leads are energized. The change in metabolic activity represents a change in the release of neurotransmitters in the brain. Such a phenomenon would not be observed with stimulation therapy because the mechanism of blocking or masking pain signals using stimulation does not affect the release of neurotransmitters.

With respect to pain processing, patients will still feel new sources of pain because the processing of pain is normalized. So if a hand is placed on a hot stove, the patient will feel the pain and pull their hand away. The use of occipital neuromodulation does not place the patient at risk of not feeling pain and acting appropriately. Pain is intended to be an "alarm system" and disabling the alarm could be detrimental.

With sources of pain that are not mechanical, that do not involve anatomical pathology such as, for example, migraines, the pain gradually improves over time. The mechanism of action has been successfully tested by trying the device on other patients who do not have migraines. Such patients include those with diseases of the nervous system such as neuropathies, reflex sympathetic dystrophy, causalgia, trigeminal neuralgia, post herpetic neuralgia, spinal cord injury, traumatic brain injury, and stroke pain. There have been patients who have undergone surgical spinal fusion surgery that did not relieve their pain. Occipital neuromodulation did relieve their pain, however.

The device has even used successfully on a patient with intractable foot pain from trauma who had six foot surgeries including fusions. There was no longer any movement in the painful area of the foot since it was fused in place with screws and plates. This patient had complete relief of his pain from occipital neuromodulation.

There has also been a patient with chronic prostatic pain. In this patient, no definable anatomical cause could be found for their pain but he both reported over 50% relief from occipital neuromodulation.

Two patients who already had spinal cord stimulators for chronic intractable neuropathic pain in the lower extremities were successfully treated with occipital neuromodulation. In both cases, spinal cord stimulation failed but occipital neuromodulation was very successful. In one of the patients the peripheral neuropathic disease had spread throughout the entire body. The patient had pain in his face and all the way down to the soles of his feet. He has enjoyed 100% relief of his pain for over six months since having an implantation of occipital neuromodulation and is off all his pain medications.

In one case, a patient who had a spinal cord injury had failed to get adequate relief with spinal cord stimulation, an intrathecal pump (spinal infusion pump), and even a deep brain stimulator. With deep brain stimulation, the same leads used in occipital neuromodulation were placed into the brain by drilling holes in the skull and placing them in the tracts where pain fibers travel. The neurosurgeons used higher amplitudes, frequencies and pulse widths compared to that used with occipital neuromodulation. Their intention was to block the pain being transmitted along these tracts of nerves. However, these regions are distant from the processing centers for pain. It was then decided to perform a test of occipital neuromodulation upon the patient since it has an entirely different mechanism of action. The patient had a positive response during his test of occipital neuromodulation. He reported that it gave him the best relief of any intervention he has had. Additional numbered examples are presented later in this specification.

Due to the ease of testing the device, it is preferable to perform a test procedure on the patients, known as the "trial phase." A single pair of leads are placed under the skin and sutured in place for approximately month. During that month's time, various frequencies and energy levels are tried to see if the patient has a positive response. The patients being treated are chronic pain patients, but they may also have other problems. The goal is a 50% reduction in pain during this trial phase. If the trial phase is successful, then the patients then undergo surgical placement of the leads under the skin. The leads are attached to an internal pulse generator (IPG), much like a pacemaker—but for pain. This is the permanent "implant phase." Patients are followed up monthly and their progress documented.

To date, over 200 patients have been treated by occipital neuromodulation in the past 5 years, which resulted in 90% success with respect to relief of pain greater than 80%. As a point of reference, the standard benchmark of successfully treating pain is a reduction of 30%. There are medical records chronicling the results and video testimony from various patients who discuss their progress and their results.

Occipital neuromodulation is different than traditional occipital nerve stimulation in a number of non-obvious ways.

First of all, the positioning of the leads is much higher up on the back of the head. The location of leads in occipital neuromodulation is anatomically unique from what is done in occipital stimulation. In occipital stimulation, the leads are always positioned at the top of the cervical spine at the level of the first or second cervical vertebra. In occipital neuromodulation, the leads are positioned off the midline at the level of an imaginary line connecting the tops of the ears. Another important difference is that the energy levels used are far smaller in occipital neuromodulation compared with occipital stimulation. The amount of energy used is so small that the patient cannot perceive it. The device is programmed so the patients do not feel the electrical impulses. They have a control box that allows them to adjust the energy output downward if they ever start to feel it. With occipital stimulation, the device is set intentionally so the patient will feel the stimulation. Stimulation feels like a tingling sensation that can be distracting or annoying. Most patients however, find it preferable to feeling pain. The tingling sensation is called paresthesia.

In occipital neuromodulation, both the amplitude of the energy and the pulse width—the time it is being delivered over—are very tiny and often at the lowest limits of what the device can perform. Furthermore, the frequencies of the electrical impulses are also at the lowest limits of what the device can perform. These parameters are far below the default settings on the device because they are not the settings normally used by practitioners. They are available, but are not used. The efficacy of this treatment at such a low amplitude, pulse width and frequency is a surprising and unexpected result. With occipital stimulation, the patient experiences pain relief within minutes and the amount of relief plateaus within the hour. With occipital neuromodulation, the patient may need a week or more to feel the onset of a change with respect to pain or the other aforementioned senses and the improvement continues to increase month by month.

The focus of this patent specification is not limited to the use of externally applied electrical signals to relieve pain via use of the occipital nerves as conduits. Other peripheral nerves can be employed as well. This mechanism of action is different, unique, and non-obvious compared to all others. This mechanism is to utilize peripheral nerves such as the occipital nerves as conduits for electrical impulses to convey them into the brain. The application of this device therefore is not limited to the occipital nerves but could be used with other peripheral nerves.

The act of "neuromodulation" involves the use of particularly weak electrical pulses that are below the parameters associated with traditional stimulation. The patients are not "stimulated." What is happening is that the electrical impulses are traveling into the brain and acting upon the processing centers for pain. With the correct frequency and pulse width, the electrical and chemical activities within these processing centers are normalized. It is known that the chemical activity is being altered as well as the electrical activity since the changes show up on functional MRI and PET scan studies. The use of this device does not block pain, per se. It normalizes the processing of pain.

Figure 2:
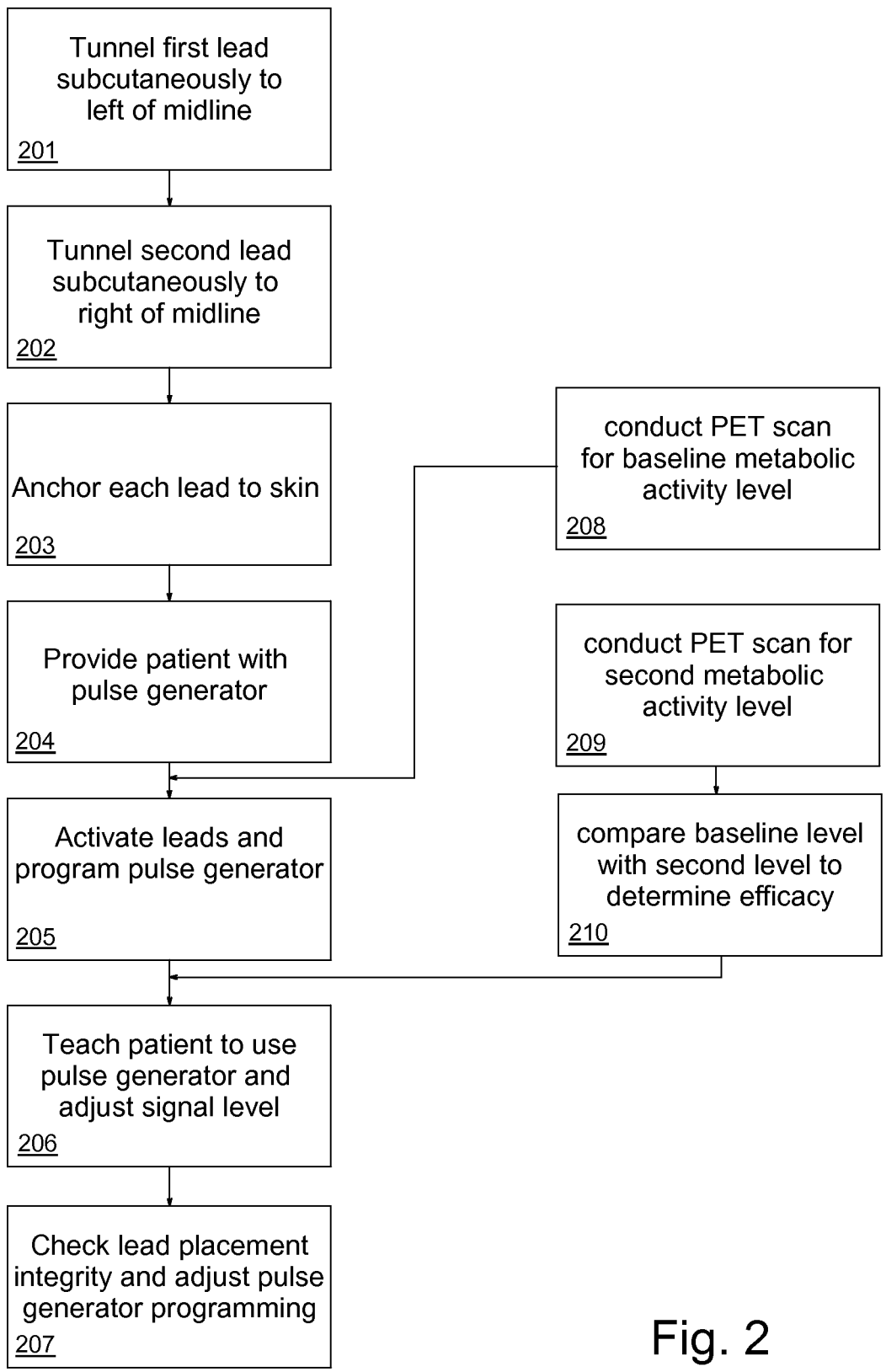
FIG. 2 is a process flow chart of the trial phase according to the present invention.
Figure 3:
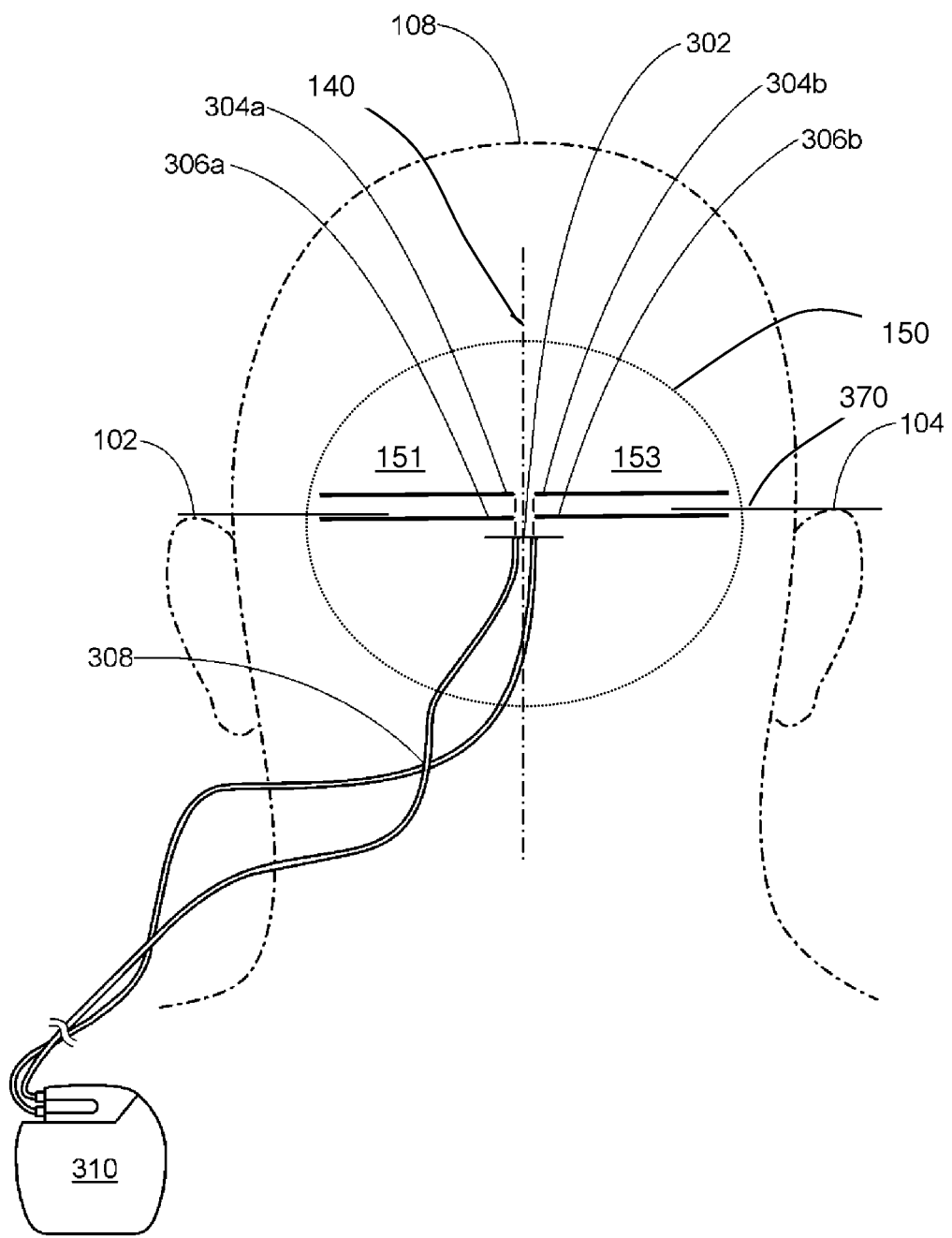
FIG. 3 shows the leads placed on a subject's head coupled with an internal pulse generator during the permanent implant phase.

Turning now to the drawings, the basic apparatus used is shown in FIG. 1, and the basic procedure of the trial phase is shown in the process flow diagram of FIG. 2. The apparatus used for the permanent implant phase is shown in FIG. 3 and its corresponding flow chart is FIG. 4.

In FIG. 1, a patient 108 has electrodes 106*a* and 106*b* positioned subcutaneously on opposite lateral portions 151, 153 of the occipital region 150 through a small incision 110 in the subject's scalp. As illustrated in FIG. 1, midline 140 divides occipital region 150 into a left lateral occipital portion 151 and a right lateral occipital portion 153. Electrodes 106*a*, 106*b* are positioned along or parallel to an imaginary line between the top of the left ear 102 and top of the right ear 104. Electrodes 106*a*, 106*b* are coupled to a pulse generator 114 with a connecting lead 112 coupled with the electrodes. One example of a suitable pulse generator and lead set is the ANS® (Advanced Neuromodulation Systems) implantable pulse generator and leads. In one embodiment, only one electrode 106 is used and it is positioned across midline 140 so that it overlies both the right and left occipital nerves.

The process flow diagram of FIG. 2 describes the basic process. In step 201, the practitioner tunnels a first lead subcutaneously to the left of the midline. In step 202, the practitioner tunnels a second lead subcutaneously to the right of the midline. Of course steps 201 and 202 can be reversed. The practitioner anchors each electrode to the skin with sutures in step 203. The patient is provided with a pulse generator in step 204, which is preferably an external pulse generator if it is for a trial phase. The leads are activated and the pulse generator is programmed in step 205. In one embodiment, the electrical signal has a current amplitude between 0.1 mA and 8 mA, frequency of 6, 12, 18, or 24 Hz, and pulse width between 50 msec and 100 msec at step 205. In another embodiment, the frequency in step 205 is from 4 Hz to 96 Hz, preferably an integer multiple of 4 Hz. The patient is taught how to use the external pulse generator and how to decrease the strength to below the threshold of perception in step 206. The electrical signal is adjusted to a level below where the subject can feel the electrode being energized, i.e. the onset of paresthesia (or tingling sensation). Decreasing the signal strength is preferably accomplished by adjusting the signal current amplitude. The pulse width may also or alternately be adjusted to reduce the signal strength below the threshold of perception.

In one embodiment, the signal has a current of 0.6 mA, frequency of 16 Hz, and pulse width of 100 msec. In another embodiment, the signal has a current of 0.6 mA, frequency of 96 Hz, and pulse width of 100 msec. It has been determined experimentally that a current of 0.6 mA or below often provides a signal that is below the threshold of perception.

The patient is examined periodically to check lead placement integrity and to adjust the pulse generator programming in step 207. If this is a trial phase, it will last approximately one month, after which time the pulse generator is shut off and the leads are removed.

An optional PET scan is conducted in step 208 to establish a first or baseline metabolic activity level for pain centers within the brain. After energizing the leads, a subsequent PET scan is conducted in step 209 to determine a second metabolic activity level for pain centers within the brain. In step 210, second metabolic activity level is compared to the baseline metabolic activity level and noting the amount of change in metabolic activity. Using the amount of change, one may determine the efficacy of the electrical signal to alter the release of neurotransmitters within the brain.

FIG. 3 shows the apparatus used for the permanent implant phase of the treatment of the present invention. If the trial phase is successful, the patient 108 is then scheduled for permanent implantation.

In FIG. 3, two pairs of leads are implanted; an upper set 304a, 304b, and a lower set 306a, 306b. An incision 302 is made along or across midline 140 of the occipital region 150. Incision 302 in one embodiment is vertical and extends along midline 140. A first pair of leads 304 has a first left lead 304a and a first right lead 304b. First left lead 304a and first right lead 304b are each positioned horizontally along an imaginary line 370 drawn between the tops of ears 102, 104. A second pair of leads 306 has second left lead 306a and second right lead 306b. Second left lead 306a and second right lead 306b are each positioned subcutaneously about 1 cm caudad (below) and substantially parallel to the first left lead 304a and first right lead 304b, respectively. The two pairs of leads 304, 306 (4 leads total) are coupled with an extension 308, which is coupled with an internal pulse generator 310.

In one embodiment, the internal pulse generator 310 is placed in a subcutaneous pocket (not shown). This subcutaneous pocket is created by the practitioner. The location of the subcutaneous pocket is variable, depending on the patient's preference. It can be over the anterior chest like a pacemaker, or it can be placed in the lower back or flank area. The practitioner creates a tunnel under the skin to connect the internal pulse generator with the leads.

In another embodiment, internal pulse generator 310 is a single unit with a battery in one of one or more of leads 304a, 304b, 306a, 306b. In this embodiment, the practitioner would have no need to tunnel an extension between the leads and a separate pulse generator 310 located in the patient's back or gluteal region, for example. Instead, each lead 304a, 304b, 306a, 306b is a matchstick-like device with a built-in pulse generator. The lead is inserted and retained subcutaneously in the patient's scalp.

Figure 4:
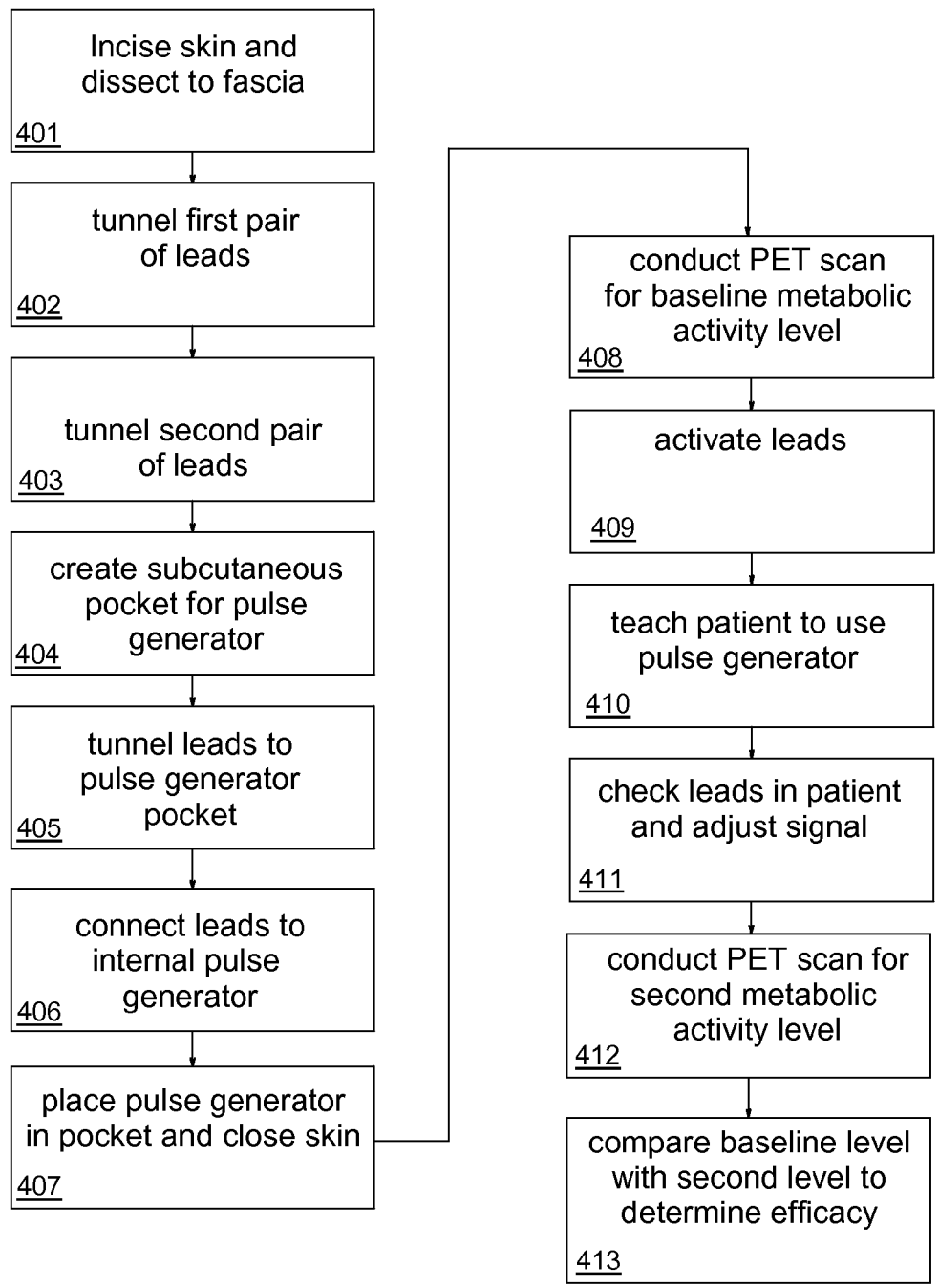
FIG. 4 is a process flow chart showing the details of the implant phase according to the present invention.

FIG. 4 is a process flow chart of the implant phase. In step 401, after the patient is anesthetized, the practitioner incises the skin and dissects down to the fascia in the midline at the level of the tops of both ears. This location is different from other procedures, where the leads are placed at the level of second cervical vertebra.

In step 402, the surgeon tunnels a first pair of leads to the left so that they are parallel to each other at a distance of approximately 1 cm apart. In step 403, the surgeon tunnels a second pair of leads to the right so that they are parallel to each other at a distance of approximately 1 cm apart. Of course, steps 402 and 403 could be reversed.

Using two sets of leads, each set having an upper lead and a lower lead, is a novel feature of the present invention. Each lead is at least at the level of the tops of the ears. A patient is instructed to alternate between the upper and lower pairs on a daily basis, or even every 12 hours (Upper leads by day, lower leads by night). Changing the location of the source of the electrical impulses enables patients to continue deriving benefit from occipital neuromodulation, since different areas are being used from month to month. This avoids a process known as "accommodation," in which the constant delivery of electrical impulses to a given area can result in a diminished response over time. The nervous system becomes accustomed to electrical energy coming from the same location over time and then becomes refractory to further influence from it.

When the pulse generator is separate from the electrodes, in step 404 the practitioner creates a subcutaneous pocket in the desired location for the internal pulse generator. In step 405, all four leads are tunneled subcutaneously to the pulse generator pocket. In step 406, the leads are connected to the internal pulse generator. In the future, the internal pulse generator could be incorporated as a single unit with the leads. In this case, subcutaneous tunneling of the leads to the internal pulse generator would not be necessary.

In step 407, the internal pulse generator is placed in its subcutaneous pocket, and the skin is closed over it with sutures and/or surgical glue. In step 409, the leads are then activated. In step 410, the patient is taught how to use the pulse generator. This step may include teaching the patient to use an external programming device to communicate with the internal pulse generator, how to use the external programming device to select present programs, and to decrease the strength of the electrical impulses to below the threshold of perception. The patient is taught to use the external programmer to decrease the signal strength so that it is strong enough to achieve the benefit sought but below the onset of paresthesia. In step 411, the practitioner follows up with the patient periodically to check the integrity of the leads and to adjust the programming, if necessary, to balance out the right and left sides, or to try a different frequency to improve the patient's response.

To determine the efficacy of occipital neuromodulation, an optional PET scan is conducted in step 408 to establish a first or baseline metabolic activity level for pain centers within the brain. As described in step 409 above, the leads are then energized with an electrical signal having amplitude between 0.1 mA and 8 mA, a frequency between 4 Hz and 96 Hz, and a pulse width between 50 msec and 100 msec. After energizing the leads, in step 412, a subsequent PET scan is conducted to determine a second metabolic activity level for pain centers within the brain. In step 413, by comparing the second metabolic activity level with the baseline metabolic activity level and noting the amount of change in metabolic activity, one may determine the efficacy of the electrical signal to alter the release of neurotransmitters within the brain. The PET scan and comparison steps are optionally included in various embodiments of a method of occipital neuromodulation.

In another embodiment, the method includes determining whether pain in a subject can be treated by occipital neuromodulation. The tips of two temporary leads are positioned subcutaneously in the occipital region of a subject's scalp with the remainder of the leads remaining outside the subject's skin. The two temporary leads are configured to conduct an electrical signal along an occipital nerve into the brain using neuromodulation. A programmer is coupled to the temporary leads and configured to deliver the electrical signal to the occipital nerve. Thus, the subject is able to adjust the electrical signal to a level such that the subject experiences a decrease in pain over time although the subject does not feel the lead being energized (below the threshold of perception).

Devices that perform occipital stimulation are programmed differently than in occipital neuromodulation. Unlike occipital stimulation, the programs of the present invention do not cycle on and off, but deliver a continuous pulsed or non-pulsed signal, such as a sine wave or a square wave.

Another difference between occipital neuromodulation and other pain treatment methods lies in the programming of each lead. It is possible to program each lead to be independent of each other in the present invention. The present invention utilizes a type of programming known as "multi-stim programming." In multi-stim programming, each lead is programmed with its own set of parameters, specifically the current amplitude being used. In this way, the actual energy being delivered to the nerve is balanced from right to left while taking into account the distance each lead is from the targeted neural tissue and the resistance that can vary from one lead to the other due to scar tissue and fibrosis. Since the mechanism of action is upon the brain and the processing centers are on both sides of the brain, it is important to the success of the treatment to maintain a balanced delivery of electrical impulses into the brain. If one side receives more electrical impulses than the other, it creates an imbalance that disrupts the equilibrium observed in a normally-functioning brain. The success rate of treatment using occipital neuromodulation has been documented at 90%, a rate which is better than other electrical methods and which demonstrates the novelty of the present invention.

Figure 5:
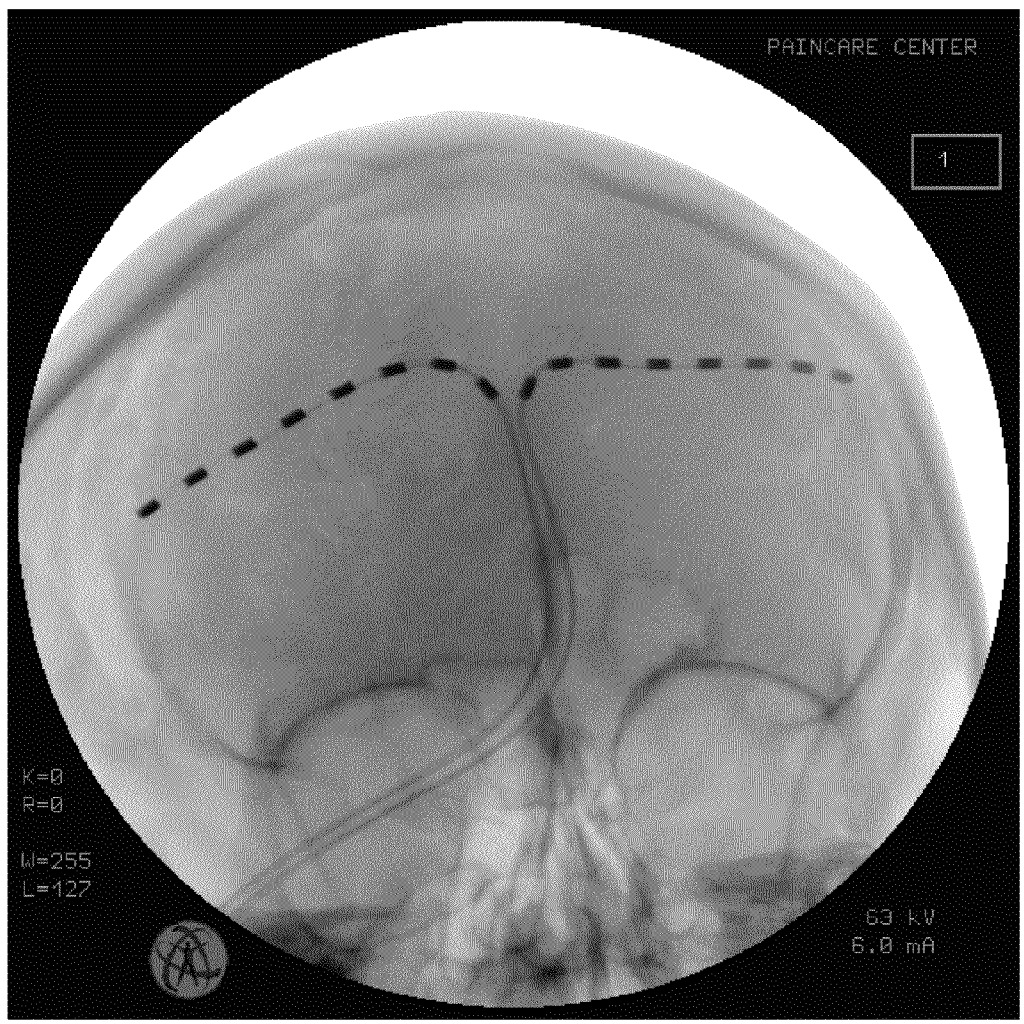
FIG. 5 is an X-ray image of electrodes and leads implanted on a subject's head according to the present invention.

FIG. 5 is an X-ray image of a pair of leads implanted within a patient. In the implant phase, two parallel leads are actually provided (4 leads total).

The method and apparatus could be provided as a kit. The kit would include at least a pair of leads, a pulse generator capable of energizing the leads with an electrical signal comprising amplitude between 0.1 mA and 8 mA; frequency between 4 Hz and 96 Hz; and pulse width between 50 msec and 100 msec. The kit also includes instructions for programming the pulse generator to generate an electrical signal effective to treat a neurological disorder, and below the level where the subject can feel the lead being energized. The instructions may cover use of the apparatus and performance of the treatment method disclosed in this specification.

As of the date of drafting this specification over 200 patients have been treated by the method of this invention in the past year and has resulted in 90% success with respect to relief of pain greater than 80%. As a point of reference, the standard benchmark of successfully treating pain is a reduction of 30%.

The following are case histories of successful treatments using the present invention.

Case #1: Patient S.B. (Migraines)

The patient is a 39 year-old female has an over 20-year history of migraines. She had seen neurologists, and had failed medication management. She got temporary relief with occipital nerve blocks and temporalis muscle injections. She underwent trial of occipital neuromodulation. On the first day of the trial, she reported 100% relief. She completed a month long trial. During that month, she had no migraines. She reported 100% relief the same day. At one month, three months, and six months she reported 100% relief of her migraines.

Case #2: Patient A.A. (Traumatic Spine Injury, Headache)

The patient is a 23 year-old male with 13-year history of headaches and neck pain after a traumatic fall which injured his cervical spine. He had been to multiple neurologists, chiropractors, and physical therapists. He obtained 30% relief from cervical facet joint injections. The patient had radiofrequency neurolysis (destruction of the nerves) of the cervical facet joints which gave him 30% relief for several weeks (much shorter duration than usual). He underwent a trial of occipital neuromodulation. After five days, he reported 75% relief. His trial lasted eight days. He then received a permanent implant. At one month, he reported 90% relief of his headaches. At three months, he reported 100% relief of his headaches. At six months, he reported 100% relief of his headaches.

Case #3: Patient R. A. (Traumatic Brain Injury, Migraine)

The patient is a 49 year-old male with history of crush injury to his skull seven years prior to considering occipital neuromodulation. An 18 pound rock fell six stories onto his head at a construction site and caved in his skull on the left side. He fell into a snow bank and was discovered approximately six hours later. He was airlifted to a trauma center where it was discovered he had bleeding in the brain, out of both ears, and his mouth. He eventually recovered but had residual symptoms. The patient suffered from constant headaches. Due to his confusion, he has been struck by motor vehicles when he wanders into the street on several occasions resulting in damage and pain in his shoulders, hips, upper back, lower back, and knees. He had failed medication management and physical therapy. He underwent a trial of occipital neuromodulation. The same day he noted 100% relief of his headaches and over the ensuing weeks, resolution of his generalized pain. The trial lasted 30 days. He went for implantation. At three days, he noted the onset of pain relief. By day 21, he was 100% pain free. At one month, three months, and six months he still reported 100% pain relief. Later, he had an accident and felt his pain and symptoms return. It was discovered that the accident had resulted in migration of his leads away from the occipital region. He underwent revision of the leads and reported 100% relief the same day and ever since.

Case #4: Patient C.S. (Fibromyalgia, Pain from Gastrointestinal Reflux Disease)

The patient is a 55 year-old female with fibromyalgia for over 25 years. She has generalized pain throughout her lower back, hips, shoulders, upper back, headaches, hands, and feet. She also had pain from GERD (esophageal reflux) and arthritis. The patient tried medications which ultimately failed due to tolerance. She also had physical therapy, acupuncture, epidural steroid injections which failed. The patient had seen several rheumatologists who had failed to relieve her pain. She underwent trial of occipital neuromodulation. In the first day, she noted onset of pain relief. By the end of her 24 day trial, she reported 90% pain decrease. This included cessation of headaches, back pain, pain in the hands and feet and a lack of pain from her GERD. She underwent implantation of the system. At one month she reported 30% relief, at three months 50% relief, and at six months 100% relief.

Case #5: A.G. (Traumatic Brain Injury, Generalized Pain, Migraines)

The patient is 50 year-old female who was involved in a motor vehicle accident. Her car was spun around and damaged on all four sides. She suffered traumatic brain injury and had constant headaches and migraines, slurred speech, and episodes of confusion. She had constant headaches and would have exacerbations for a week at a time during which she was sensitive to light, sound, nauseous, and had stroke-like symptoms of disorientation and increased slurred speech. Her headaches were usually one side or the other and when she had them she could not see out of the eye on the same side as the headache. Her MRI and CT scan of the brain were negative for any active pathology. She also suffered from chronic neck pain from whiplash injury, and felt diffuse achy pain throughout her body. She had failed medications and physical therapy. She underwent a trial of occipital neuromodulation. After five days, she noted improvement in her pain. At the end of her 30-day trial, she reported 80% relief of her pain. She underwent implantation of occipital neuromodulation. At one month she reported 90% pain relief and came off her medications. She then picked at her incision site and infected herself. The system was removed. After the system was removed, her pain and other symptoms returned in full force. Another system was implanted once the infection cleared. Again she reported 90% relief. Unfortunately she again picked at her incision site and infected herself again. The system was removed a second time and has not been replaced out of concern she will infect herself again.

Case #6: C.B. (Migraines)

The patient is a 75 year-old man. He had intractable daily migraines for over 35 years. He had seen multiple neurologists and pain centers. He was on high dose opioid analgesics since all other medication had failed to adequately relieve his pain. He obtained excellent relief from occipital nerve blocks. The patient underwent a trial of occipital neuromodulation. On the first day, he noted the onset of pain relief. At the end of the fifteen day trial, he noted 100% relief of his migraines and was able to reduce his medications dramatically. He underwent implantation of occipital neuromodulation. At one month he had 100% relief, at three months 100% relief, and at six months 100% relief. After that he developed chest pain and had emergency open heart surgery. While being transferred off the operating room table, his leads became dislodged. This was discovered when he woke up from the anesthesia and had a terrible migraine. An X-ray showed the leads were no longer in the occipital region. When he was stable, he underwent revision of the leads and again reported 100% relief which is has been for four months since the revision.

Case #7: Patient L.J. (Charcot-Marie-Tooth Disease (Peripheral Neuropathy), Gout, Inadequate Relief from Spinal Cord Stimulation)

The patient is a 64 year-old man with a 25-year history of peripheral neuropathy diagnosed as Charcot-Marie-Tooth disease along with gout affecting his feet. Three years prior to considering occipital neuromodulation, he underwent a trial and implantation of a spinal cord stimulator which gave him 30% pain relief for his lower extremity pain. But then his disease spread and he then had pain in his face, upper extremities, and the lower extremities. The spinal cord stimulator was unable to reach those higher areas of pain so it was rendered fairly useless. He still needed high dosages of neuropathic pain medications. He had been to several neurologists and rheumatologists over the years. He underwent a trial of occipital neuromodulation. On the first day he noted relief of his pain. He turned off his spinal cord stimulator to see how effective the occipital neuromodulation was. At the end of a seventeen day trial, he reported 100% pain relief throughout his entire body—from the face and upper extremities, down to his toes. He then underwent implantation of occipital neuromodulation. After one month he reported 100% pain relief, at three months 100%, and at six months 100%. He also was weaned off all his pain medications completely. Then about a month later, he reported over a period of several days, his pain had returned in full force. An X-ray of the leads showed they had moved away from the occipital region which explained the return of his pain. He underwent a revision of the leads and again within the first month reported 100% pain relief. He has been doing well since then.

Case #8: Patient M.W. (Migraines, Post Stroke Pain)

The patient is a 45 year-old female. She has a 34 year history of chronic migraines. She has seen over ten neurologists and had been tried on dozens of medications with inadequate relief. She also tried physical therapy, acupuncture, occipital nerve blocks—gave temporary relief. When in labor at the age of 28, she suffered a stroke and this exacerbated her migraines and gave her pain in the right side of her body (upper and lower extremities). CT scans, MRI scans and EEG studies were negative for any active pathology. She underwent a trial of occipital neuromodulation. She reported the onset of relief at one day and at the end of the 22 day trial, she reported over 90% pain relief. She then underwent implantation of occipital neuromodulation. At one month she reported over 90% relief, at three months over 90% relief.

Case #9: Patient K.K. (Spine Trauma, Lumbar Spinal Stenosis, Migraine, Fibromyalgia)

The patient is a 40 year-old female. She has a history of falling down stairs, causing damage to the spine and knees. She has a neurogenic bladder (loss of bladder control) from the damage to the spine. She had three operations on her right knee and has had chronic back pain which responded partially to lumbar epidural steroid injections. An MRI showed lumbar spinal stenosis. She also has a history of migraine which responded temporarily to occipital nerve blocks. She also has history of fibromyalgia for over 20 years resulting in diffuse pain throughout her neck, shoulders, arms, back, hips, legs. She failed to obtain adequate relief despite high dosages of methadone and other medications for her pain. She underwent trial of occipital neuromodulation. She reported the onset of relief beginning after three hours. By the end of the 12 day trial, she reported 100% relief of her migraines, generalized pain in the upper and lower extremities, back pain. She then underwent implantation of occipital neuromodulation. At one month she reported 100% relief, at two months she reported 100% relief. She continues to do well.

Case #10: Patient L.C. (Fibromyalgia, Neck Pain)

The patient is a 59 year-old woman diagnosed with fibromyalgia. She had lower back pain radiating down to her feet along with restless leg syndrome. She was rear-ended in a motor vehicle accident which resulted in chronic neck pain and headaches along with upper extremity pain. She failed physical therapy. She had some relief from lumbar epidural steroid injections and trigger point injections into the trapezius muscles. MRI showed lumbar degenerative disc disease with one prominent bulge. A following MRI showed cervical spinal stenosis. She was not considered a candidate for surgery since there were no signs of nerve root compression. She failed to obtain relief despite physical therapy and high potency opioids. She underwent a trial of occipital neuromodulation. She reported the onset of relief beginning on the first day. By the end of the 12 day trial, she reported 90% relief of her headaches, neck pain, back pain, extremity pain. She also reported improvement in mood, energy levels, and sleep. She then underwent implantation of occipital neuromodulation. At one month she reported 100% relief, at three months 100% relief.

Case #11: Patient L.E. (Parkinson's Disease, Temperomandibular Joint Disorder—TMJ Disorder)

The patient is a 53 year-old woman with history of Parkinson's disease. The constant muscle jerking caused her to develop back pain radiating down the legs to the feet and hips. An MRI showed multilevel misalignment of the lumbar spine along with degenerative changes. Her back pain did not respond to lumbar epidural steroid injections and she had to stop working due to pain. She was put on opioids for pain and her dose escalated over time. She saw a neurologist who was unsuccessful in improving her Parkinson's and her pain continued to escalate. She could no longer have an MRI due to her inability to hold still. Her pain ascended up her back to her neck and head causing severe constant headaches. She had severe temperomandibular joint pain which triggered headaches as well. She developed acute sensitivity to touch from her neck down to her back as her nervous system became sensitized to pain. She saw a neurosurgeon who said there were no surgical options. Despite high dosages of opioids and steroid, there was no change. She underwent a trial of occipital neuromodulation. On the first day she noted the onset of relief. At the end of the seven day trial, she noted 90% relief of her pain, improvement in mood and sleep, and reduced Parkinsonian movements. She was supposed to have the implantation of occipital neuromodulation performed but due to family issues moved out of the area and was lost to follow up.

Case #12: Patient C.L. (Migraines, Fibromyalgia, Lumbar Radiculopathy)

The patient is a 48 year-old female with over a 20-year history of migraines, fibromyalgia, and back pain radiating down the lower extremities. She was on escalating dosages of opioids for her pain and lost control of her ability to take them as prescribed. Her dose needed to be forcibly reduced. She reported excellent but temporary relief with lumbar epidural steroid injections. Originally the intention was to perform a trial of spinal cord stimulation but in light of her migraines and fibromyalgia, a trial of occipital neuromodulation was performed instead. She reported the onset of relief beginning the first day during the trial. By the end of the 30-day trial, she reported 100% pain relief and had decreased her dose of medications dramatically. She then underwent implantation of occipital neuromodulation. At one month she reported 30% relief due to residual surgical pain. At three months she reported 95% relief. Sometime during the fifth month, she reported her pain was returning. An X-ray of the leads showed they had migrated. She is scheduled for revision of the leads and her medications have been increased to compensate for the loss of relief from occipital neuromodulation.

Case #13: Patient P.P. (Chronic Prostatitis and Pelvic Pain)

The patient is a 55 year-old male with a history of chronic prostatitis for over ten years. He has traveled the world including to Philadelphia and the Philippines seeking relief for his pelvic pain. He underwent the implantation of an intrathecal spinal infusion pump to deliver pain medications directly to his spinal cord to relieve his pain. But despite multiple medications used in the pump, he never had adequate relief. He was also taking a high dose of oral opioids as well. The patient had a nerve block performed to block the prostate but it did not alleviate his pain. He then underwent surgical revision of the intrathecal pump catheter hoping that moving it to a lower spot of his spinal cord would prove more effective for his pain, but it was not. After a year and a half the decision was made to try occipital neuromodulation. A trial of occipital neuromodulation was performed. The patient noted onset of relief after 20 days. By the end of the 30-day trial, he reported 90% pain relief and had improved mood and sleep. He has not had the implantation of occipital neuromodulation performed since he recently underwent spinal fusion surgery for lumbar nerve root compression which recently developed. He needs to recover from that surgery before having any further surgery.

Case #14: Patient J.C. (Motor Vehicle Accident Resulting in Fracture of 50 Bones, Foot Pain after Five Corrective Foot Surgeries, Shoulder Pain after 4 Corrective Shoulder Surgeries, Headaches)

The patient is a 44 year-old male who had a severe motor vehicle injury. He broke 50 bones in his body and was paralyzed from the neck down for eight days. His right shoulder was replaced and he had three more shoulder operations to correct the anatomical abnormalities. He also underwent five right foot operations including fusions with screws and plates. He gets temporary relief from shoulder injections and injections into the lumbar facet joints. He is on a high dose of opioids and muscle relaxants for his pain. Occipital nerve blocks gave temporary relief of his headaches. He underwent a trial of occipital neuromodulation. He reported pain relief the first day. By the end of the 30-day trial, he had 100% relief of his right foot pain and headaches. He reported 75% relief of his right shoulder. He then underwent implantation of occipital neuromodulation. At one month he reported 100% pain relief in the above areas. At three months he reported 100% pain relief in the above areas.

Case #15: Patient B.H. (Trigeminal Neuralgia—Post Herpetic, Lumbar Pain from Disc Degeneration and Arthritis, Bilateral Thumb Pain from Arthritis)

The patient is a 75 year-old woman with a history of postherpetic trigeminal neuralgia for one year. She had blocks of various cranial nerves and the stellate sympathetic ganglion with limited relief. She failed medication management. She also had bilateral thumb pain from arthritis. She underwent a trial of occipital neuromodulation. She reported the onset of relief at five days. At the end of the 30-day trial, she reported 75% relief of the trigeminal neuralgia pain, 100% relief of her back and thumb pain. She then underwent implantation of occipital neuromodulation. At one month she reported 80% overall relief. At three months she reported 98% overall relief.

Case #16: Patient C.G. (Cervical Postlaminectomy Syndrome, Lumbar Postlaminectomy Syndrome, Fibromyalgia)

The patient is a 45 year-old female. She has a twenty year history of fibromyalgia causing generalized pain and a two year history of cervical and lumbar postlaminectomy syndrome (had cervical and lumbar spine surgery with inadequate relief of neck and back pain). She had failed medication management, physical therapy, injections. She underwent a trial of occipital neuromodulation. She reported the onset of relief the same day as the trial began. At the end of the 25-day trial, she reported 100% pain relief. She then underwent implantation of occipital neuromodulation. At one month she reported 85% pain relief. At three months she reported 85% pain relief.

Case #17: Patient K.W. (Hemiplegic Migraines)

The patient is a 49 year-old female with a 30-year history of hemiplegic migraines. When she gets a migraine she has the symptoms of a stroke (weakness of the left side of her body). She had failed medication management. MRI and CT scans were negative for any pathology. She underwent a trial of occipital neuromodulation. She reported the onset of relief after five days. At the end of a 30-day trial, she reported 50% pain relief. She then underwent implantation of occipital neuromodulation. At one month she reported 50% pain relief. At three months she reported 75% pain relief.

Case #18: Patient J.C. (Ankylosing Spondylitis, Cervical Radiculopathy, Thoracic Radiculopathy, Lumbar Radiculopathy)

The patient is a 51 year-old female with over a 20-year history of ankylosing spondylitis (bamboo spine) with pain from her head down her back and involving her arms and legs. She had lumbar fusion in the past which did not alleviate her back pain. She had an intrathecal spinal infusion pump which was not helping her pain despite increasing dosages of narcotics and muscle relaxants in the pump. She had pain constantly during the day when moving about and at night when she tried to sleep but could not sleep due to pain. The patient underwent a trial of occipital neuromodulation. She reported the onset of relief after seven days. At the end of a 30-day trial, she reported 100% relief of her pain when at rest and was able to sleep through the night for the first time in over 20 years. She was going to go for implantation of occipital neuromodulation but has developed worsening cervical spinal stenosis which will require surgical intervention.

Case #19: Patient A.B. (Cluster Headaches, Migraines, Fibromyalgia)

The patient is a 62 year-old female with over a 50-year history of cluster headache and migraines. She developed fibromyalgia 15 years ago. She had failed medication management and holistic approaches. MRI and CT scans failed to show any pathology. She underwent a trial of occipital neuromodulation. She reported the onset of relief after one day. At the end of the 30-day trial, she reported 85% pain relief and resolution of her aphasia. She is on the schedule for implantation of occipital neuromodulation.

Case #20: Patient B.P. (Chiari Malformation, Intracranial Aneurysms, Migraines, Fibromyalgia, Back Pain, Bilateral Morton's Neuroma, Osteoarthritis Hip, Irritable Bowel Syndrome with Abdominal Pain)

The patient is a 64 year-old woman with chronic pain for over 35 years. She developed an anatomical abnormality in the brainstem called a Chiari malformation along with intracranial aneurysms. She had chronic migraines and despite intracranial surgery and decompression of her brainstem, continued to experience her migraines and generalized pain throughout her body. She also developed back pain from spinal degeneration and had pain in her feet from Morton's neuromas in her feet. She also had hip pain from osteoarthritis. She had failed medications, physical therapy, and injections. MRI and CT scans showed no surgically addressable pathology. She underwent a trial of occipital neuromodulation. She reported the onset of relief after ten days. By the end of a 30-day trial, she reported 90% pain relief of her migraines, generalized pain from the fibromyalgia, her back pain, her bilateral foot pain. Her abdominal pain from irritable bowel syndrome was 100% relieved. She is scheduled for implantation of occipital neuromodulation.

Case #21: Patient P.R. (Peripheral Neuropathy from the Knees Down Due to Peroneal Nerve Entrapment, Fibromyalgia, Neck Pain, Back Pain, Migraine)

The patient is a 55 year-old woman with a 15-year history of chronic pain. She suffers pain in all her major joints from fibromyalgia. She also has documented peroneal nerve entrapment by EMG (electromyography), and migraines. She was going to go for peripheral nerve surgery to release the entrapped peroneal nerves. She underwent a trial of occipital neuromodulation first. She reported the onset of relief after one day but only of the pain above her knees along with improvement in mood, sleep, and energy. At the end of her 30-day trial, she reported 100% relief of all pain above the knees. As for the pain below the knees, she reported 100% relief when at rest and 40% otherwise. The peripheral nerve surgeon recommended she have the implantation of occipital neuromodulation first to see how she does since it may obviate the need to perform peripheral nerve surgery. She is scheduled for implantation of occipital neuromodulation.

Case #22: Patient P.B. (Reflex Sympathetic Dystrophy Lower Extremities, Inadequate Relief with Spinal Cord Stimulation, Lumbar Postlaminectomy Syndrome)

The patient is a 45 year-old man who had a skiing accident. He fractured his lumbar vertebrae and shattered both his heels. Despite lumbar laminectomy and fusion along with fusion of his feet, he continued to have severe pain. He underwent a trial and implantation of a spinal cord stimulator. As time went on, the spinal cord stimulator failed to give him adequate relief. He underwent a series of ketamine infusions in the hospital to relieve his pain for weeks at a time. Over time, the ketamine infusions yielded diminishing relief. He underwent a trial of occipital neuromodulation. He reported the onset of relief on the fifth day and turned off his spinal cord stimulator. At the end of his 10-day trial, he reported 70% pain relief. He then underwent implantation of occipital neuromodulation. Within a week of surgery, the patient is already reporting 50% pain relief without the use of his spinal cord stimulator.

Case #23: Patient W.C. (Cervical Spine Trauma, Brachial Plexopathy, Migraines)

The patient is a 38 year-old man who slipped and fell causing damage to his cervical spine and brachial plexus which required surgery. Despite the surgery, he had severe neck pain radiating up to his head and down his right arm and hand. He had frequent episodes without warning which resulted in the loss of sensation and power in the right arm and hand. Since he worked as a professional chef, he started injuring himself by accident with knives and had to stop working. He failed to get relief with medications and physical therapy plus holistic approaches. He underwent a trial of occipital neuromodulation. He reported the onset of relief on the fifth day. At the end of the 30-day trial, he reported over 50% relief of his pain. He is strongly considering going for implantation of occipital neuromodulation.

Case #24: Patient D. M. (Spinal Cord Transection at T7, Failed Spinal Cord Stimulation Trial, Failed Deep Brain Stimulation Trial and Implantation)

The patient is a 48 year-old man who fell off his roof and suffered transection of his spinal cord at T7. He became immediately paraplegic, has pain in the mid back radiating down to his toes, and has no control over his bowel or bladder function. He had emergency spine surgery to pick the fragments of shattered bone out of his spine and the remaining intact bones were fused with rods and screws. Medications and physical therapy along with holistic medicine failed to relieve his back and lower extremity pain. He underwent a trial of spinal cord stimulation but that did not affect his pain. He then underwent a trial of deep brain stimulation (had electric leads surgically placed into his brain). He was awoken from anesthesia to test the deep brain stimulator but had no relief. Since the electric leads were already in place, the neurosurgeon closed his skull and left them in place. Despite postoperative reprogramming over six months, he never had any relief. The device was turned off and left inert. He underwent a trial of occipital neuromodulation. He reported the onset of pain relief on the fourteenth day. The trial ended inadvertently on the twenty-first day when one of the leads became dislodged. He reported 30% pain relief—the best he had ever experienced.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

I claim:

1. A method of treating pain in a subject comprising the steps of:
   positioning a tip of at least one lead subcutaneously in an occipital region of a subject's scalp substantially along an imaginary line connecting the tops of the subject's ears, the at least one lead configured to conduct an electrical signal along an occipital nerve into the brain; and
   energizing the at least one lead to conduct the electrical signal along the occipital nerve into the brain; and
   adjusting the electrical signal to a level effective to decrease the subject's pain over time and wherein the subject cannot feel the lead being energized; and
   maintaining the level of the electrical signal below a threshold of perception for at least a month.

2. The method of claim 1 wherein the electrical signal comprises:
   a current between 0.1 mA and 8 mA;
   a frequency between 4 Hz and 96 Hz; and
   a pulse width between 50 msec and 100 msec.

3. The method of claim 2, wherein the current is 0.6 mA or below.

4. The method of claim 3, wherein the frequency is 16 Hz and the pulse width is 100 msec.

5. The method of claim 3, wherein the frequency is 96 Hz and the pulse width is 100 msec.

6. The method of claim 1, wherein the electrical signal alters the release of one or more neurotransmitters within the brain, the one or more neurotransmitters selected from the group consisting of dopamine, serotonin, GABA, acetylcholine, and substance P.

7. The method of claim 1, wherein the pain is one selected from the group consisting of migraine pain, fibromyalgia pain, neuropathic pain, and traumatic brain injury pain.

8. A method of treating pain in a subject comprising the steps of:
    positioning a tip of at least one lead subcutaneously in an occipital region of a subject's scalp, the at least one lead configured to conduct an electrical signal along an occipital nerve into the brain; and
    energizing the at least one lead to conduct the electrical signal along the occipital nerve into the brain; and
    adjusting the electrical signal to a level effective to decrease the subject's pain over time and wherein the subject cannot feel the lead being energized;
    wherein the at least one lead comprises:
        a first pair of leads having a first left lead and a first right lead, wherein the first left lead and the second left lead are positioned in opposite lateral occipital portions of the occipital region of the subject's scalp and along an imaginary line connecting the tops of the subject's ears; and
        a second pair of leads having a second left lead and a second right lead, the second pair of leads positioned below and substantially parallel to the imaginary line and wherein the second left lead and the second right lead are positioned in opposite lateral occipital portions of the occipital region of the subject's scalp.

9. A method of treating pain in a subject comprising the steps of:
    positioning a tip of at least one lead subcutaneously in an occipital region of a subject's scalp, the at least one lead configured to conduct an electrical signal along an occipital nerve into the brain, wherein the at least one lead comprises:
        a first temporary lead positioned in a first lateral occipital region substantially along an imaginary line connecting the tops of the subject's ears; and
        a second temporary lead positioned in a second lateral occipital region opposing the first lateral occipital region and substantially along the imaginary line;
    energizing the at least one lead to conduct the electrical signal along the occipital nerve into the brain;
    adjusting the electrical signal to a level effective to decrease the subject's pain over time and wherein the subject cannot feel the lead being energized, wherein the electrical signal comprises a current between 0.1 mA and 8 mA, a frequency between 4 Hz and 96 Hz, and a pulse width between 50 msec and 100 msec; and
    coupling a programmer to the at least one lead, the programmer being capable of delivering the electrical signal to the occipital nerve, thereby enabling the subject to adjust the electrical signal to a level such that the subject experiences a decrease in pain over time although not being able to feel the lead being energized.

10. The method of claim 9, further comprising the steps of:
    implanting a first pair of permanent leads having a first left lead and a first right lead, wherein the first left lead and the first right lead are positioned in opposite lateral portions of the occipital region of the subject's scalp and along an imaginary line connecting the tops of the subject's ears; and
    implanting a second pair of permanent leads having a second left lead and a second right lead, the second pair of permanent leads positioned below and substantially parallel to the imaginary line and wherein the second left lead and the second right lead are positioned in opposite lateral occipital portions of the occipital region of the subject's scalp;
    implanting an internal pulse generator subcutaneously; and
    coupling the first pair of permanent leads and the second pair of permanent leads to the implanted internal pulse generator.

11. The method of claim 9, further comprising the steps of:
    conducting a PET scan prior to the energizing step to establish a first metabolic activity level for pain centers within the brain;
    conducting a subsequent PET scan after the energizing step to determine a second metabolic activity level for pain centers within the brain;
    comparing the second metabolic activity level with the first metabolic activity level to determine a change in metabolic activity.

* * * * *